(12) United States Patent  
Robinson et al.

(10) Patent No.: US 8,117,253 B2  
(45) Date of Patent: Feb. 14, 2012

(54) CONDITION CONTROL SYSTEM, DEVICE AND PROCESS FOR MESSAGE TRANSMISSION

(75) Inventors: Julien Robinson, Le Plessis-Robinson (FR); Mathieu Boussard, Chailly-en-Biere (FR); Denis Leclerc, Igny (FR); Fabien Bataille, Massy (FR); Abdelkrim Hebbar, Orsay (FR); Bruno Mongazon-Cazavet, St Michel-sur-Orge (FR)

(73) Assignee: Alcatel Lucent, Paris (FR)

( * ) Notice: Subject to any disclaimer, the term of this patent is extended or adjusted under 35 U.S.C. 154(b) by 0 days.

(21) Appl. No.: 11/574,977

(22) PCT Filed: Mar. 2, 2007

(86) PCT No.: PCT/FR2007/050869  
§ 371 (c)(1),  
(2), (4) Date: Jan. 12, 2009

(87) PCT Pub. No.: WO2007/101959  
PCT Pub. Date: Sep. 13, 2007

(65) Prior Publication Data  
US 2009/0119360 A1 May 7, 2009

(30) Foreign Application Priority Data

Mar. 6, 2006 (EP) ..................................... 06300204

(51) Int. Cl.  
*G06F 15/16* (2006.01)  
*H04W 4/00* (2009.01)  
*H04Q 9/00* (2006.01)  
*G06Q 10/00* (2006.01)

(52) U.S. Cl. ........ 709/202; 709/203; 709/206; 455/466; 340/5.52; 705/2

(58) Field of Classification Search .......... 709/201–207, 709/249; 455/426, 466; 340/825.69; 705/2  
See application file for complete search history.

(56) References Cited

U.S. PATENT DOCUMENTS 6,970,098 B1 * 11/2005 Adams et al. ............ 340/825.69  
(Continued)

*Primary Examiner* — Ian N Moore  
*Assistant Examiner* — Kiet Tang  
(74) *Attorney, Agent, or Firm* — Fay Sharpe LLP

(57) ABSTRACT

The invention concerns in particular a system comprising: a first terminal (1); a second terminal (21 or 22 or 23); at least a first messaging system (31 or 32 or 33) able to transmit, to the second terminal, at least the message body of a message (10) from the first terminal; at least one device (4) controlling at least one condition (11), at least once, the said control device allowing the first messaging system to transmit to the second terminal at least the message body of the said message if the condition control result is positive, the said control device preventing the first messaging system from transmitting to the second terminal at least the message body of the said message if the condition control is negative, at least during the time for which the condition control result remains negative; at least one data server (51 or 52 or 53 or 54) external to the control device; at least one link providing communication through the Internet between on the hand the external server, or at least one of the external servers, and on the other hand the control device, the condition control device being designed to: store a message sent by the first terminal; receive at least one item of information from at least one external server; at least partially perform the condition control relating to the said message stored by means of the information received from the external server.

15 Claims, 2 Drawing Sheets

U.S. PATENT DOCUMENTS

| | | | |
|---|---|---|---|
| 2002/0023138 A1* | 2/2002 | Quine et al. | 709/206 |
| 2002/0173304 A1* | 11/2002 | Horompoly | 455/426 |
| 2003/0097280 A1* | 5/2003 | Fitzpatrick et al. | 705/2 |
| 2004/0177110 A1* | 9/2004 | Rounthwaite et al. | 709/202 |
| 2004/0249984 A1* | 12/2004 | Das et al. | 709/249 |
| 2005/0089019 A1 | 4/2005 | Salim et al. | |
| 2005/0186978 A1* | 8/2005 | Lin | 455/466 |
| 2006/0235925 A1* | 10/2006 | Rossotto et al. | 709/203 |

* cited by examiner

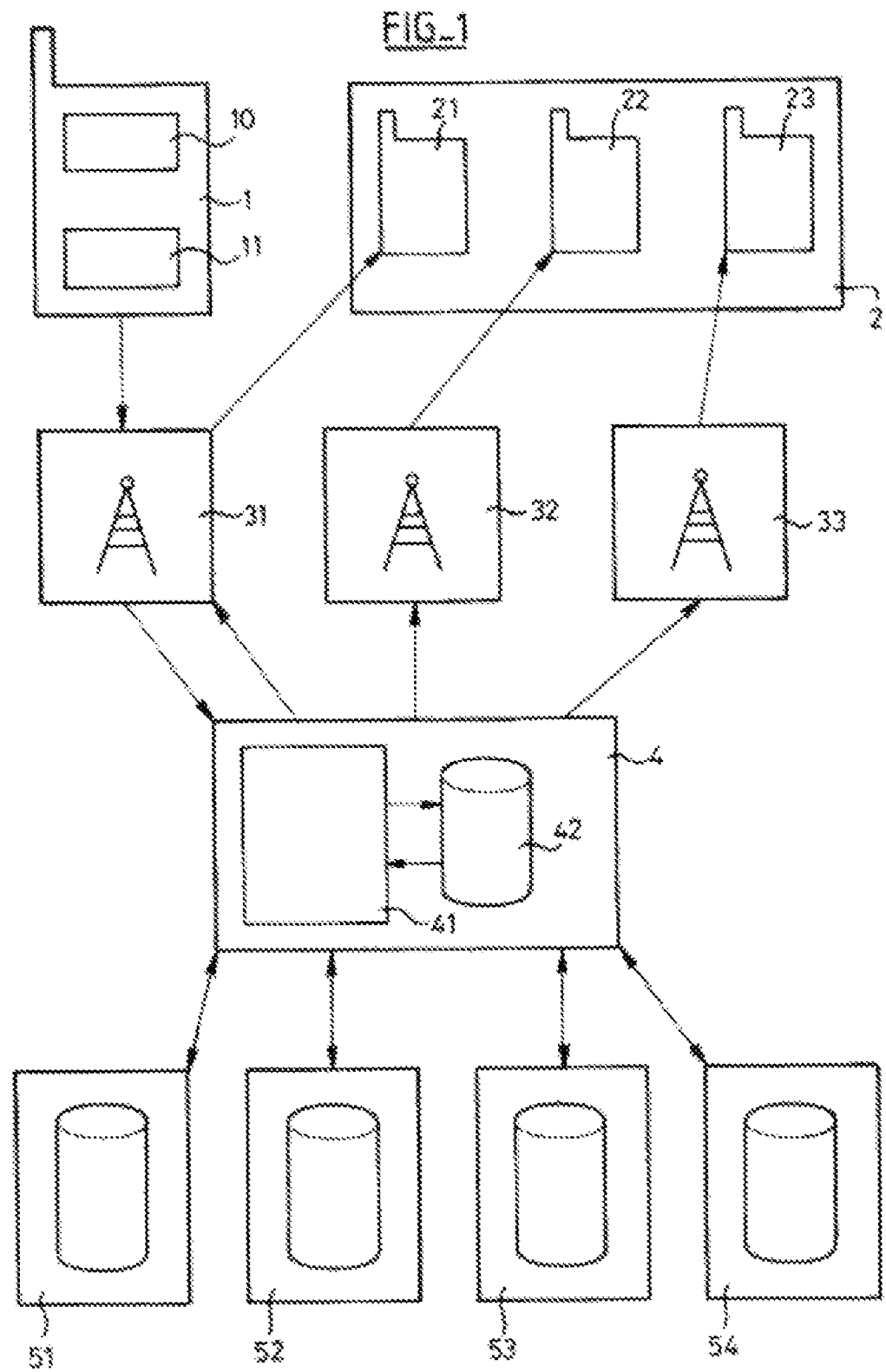

FIG_2
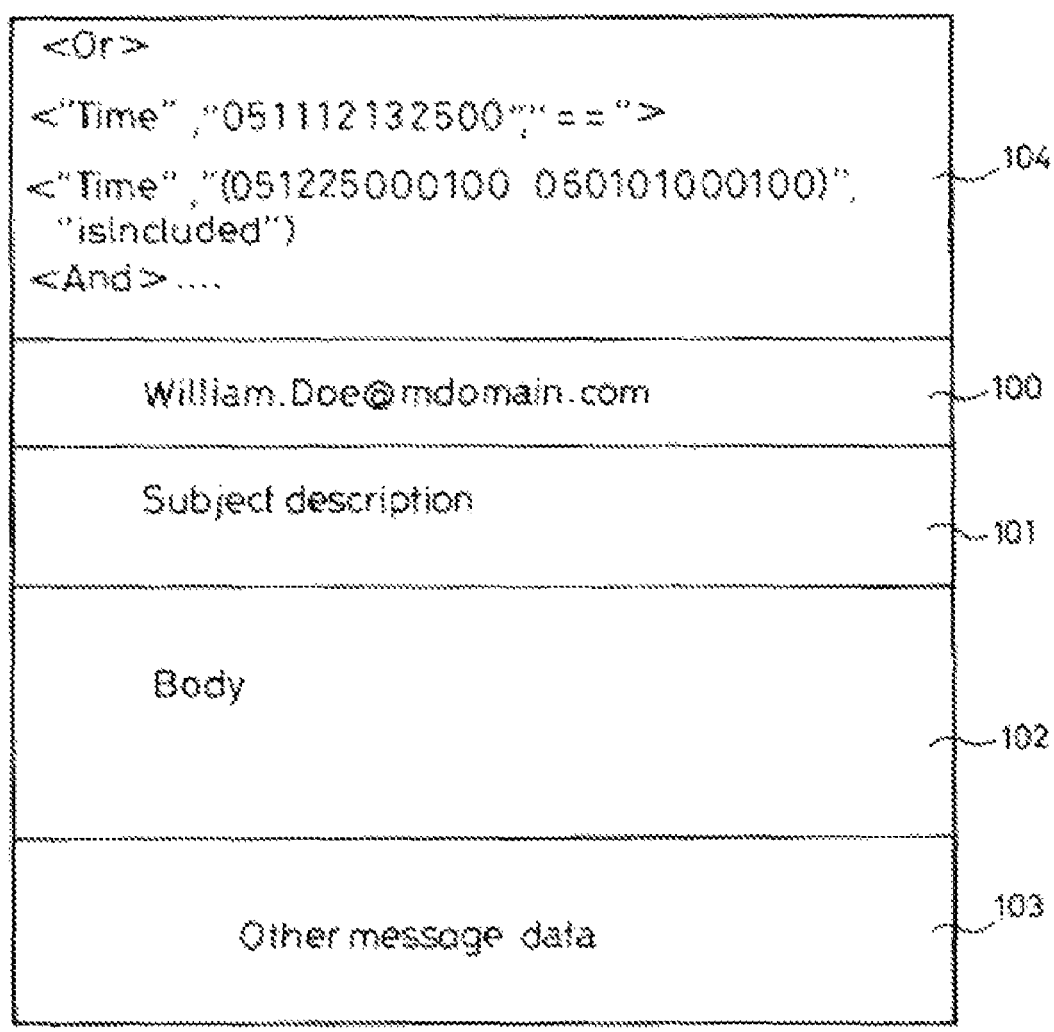

CONDITION CONTROL SYSTEM, DEVICE AND PROCESS FOR MESSAGE TRANSMISSION

The invention concerns the field of condition control systems, devices and processes for the transmission of messages to their recipients. The condition, or at least one of the conditions, is preferably connected to the context of the user receiving the message.

According to a first previous state of the art, such as that described in US patent 2005/0186978, a condition control device is known, but this control is purely internal; indeed, it does not call on a data server external to the control device.

According to a second state of the art, such as that described in application 2002/0173304, a device for transmitting an alert message to data servers external to the device for transmission to terminals is known; however, the condition control for alert message transmission does not call on information obtained from an external data server, which for its part would be separate from the alert message itself.

The invention proposes the capacity to perform a condition control before the transmitting of a message to a recipient, by means of at least one item of information obtained from a data server external to the control device and the transmitting terminal, with the external information used for the control not therefore coming either from the message to be controlled or the control device itself. This entails greater flexibility and a larger variety in the types of condition that may be attached to a message to allow its transmission.

The invention concerns the control system, the control device and the control process. The control system and the control device may be implemented separately, by means of a control device separate from the messaging system(s), or by means of at least one control device integrated in a messaging system in the form of an application layer of the said messaging system. Each messaging system, if there are several, may therefore have its own control application layer.

According to the invention, a system is envisaged comprising: a first terminal; a second terminal; at least a first messaging system able to transmit, to the second terminal, at least the message body of a message from the first terminal; at least one device controlling at least one condition, at least once, the said control device allowing the first messaging system to transmit to the second terminal at least the message body of the said message if the condition control result is positive, the said control device preventing the first messaging system from transmitting to the second terminal at least the message body of the said message if the condition control is negative, at least during the time for which the condition control result remains negative; characterized in that the system also comprises: at least one data server external to the control device; at least one link providing communication through the Internet between, on the one hand, the external server or at least one of the external servers, and on the other hand the control device; and in that the condition control device is designed to: store a message sent by the first terminal; receive at least one item of information from at least one external server; at least partially perform the condition control relating to the said message stored by means of the information received from the external server.

According to the invention, a system is also envisaged comprising: a first terminal; a second terminal; at least a first messaging system able to transmit, from the first terminal to the second terminal, at least the message body of a message, and including an application layer for controlling at least one condition, at least once; the said control application layer allowing the first messaging system to transmit to the second terminal at least the message body of the said message if the condition control result is positive, the said application layer preventing the first messaging system from transmitting to the second terminal at least the message body of the said message if the condition control is negative, at least during the time for which the condition control result remains negative; characterized in that the system also comprises: at least one data server external to the first messaging system; at least one link providing communication through the Internet between, on the one hand, the external server or at least one of the external servers, and, on the other hand, the first messaging system; and in that the condition control application layer is designed to: store, or have stored by the first messaging system, a message sent by the first terminal; receive at least one item of information from at least one external server; at least partially perform the condition control relating to the said message stored by means of the information received from the external server.

The invention also envisages a device for controlling at least one condition, at least once, designed to: allow a messaging system to transmit to a terminal at least the message body of a message sent by another terminal if the condition control result is positive; prevent a messaging system from transmitting to a terminal at least the message body of a message sent by another terminal if the condition control result is negative, at least during the time for which the condition control result is negative; characterized in that the control device is also designed to: be linked through the Internet to at least one data server external to the control device; and in that the condition control device is also designed to: store a message sent by a first terminal; receive at least one item of information from at least one external server; at least partially perform the condition control relating to the said message stored by means of the information received from the external server.

The invention further envisages an application layer for controlling at least one condition, at least once, intended to be integrated in a messaging system, designed to: allow a messaging system to transmit to a terminal at least the message body of a message sent by another terminal if the condition control result is positive; prevent a messaging system from transmitting to a terminal at least the message body of a message sent by another terminal if the condition control result is negative, at least during the time for which condition control result remains negative; characterized in that the control application layer is also designed to: be linked through the Internet to at least one data server external to the control application layer; and in that the condition control application layer is also designed to: store, or have stored by a messaging system, a message sent by a terminal; receive at least one item of information from at least one external server; at least partially perform the condition control relating to the said message stored by means of the information received from the external server.

The invention also envisages a process for controlling at least one condition, at least once, comprising: a condition control stage which, in the case of a positive condition control result, allows a messaging system to transmit to a terminal at least the message body of a message sent by another terminal, and which, if the condition control result is negative, prevent a messaging system from transmitting to a terminal at least the message body of a message sent by another terminal, at least during the time for which the condition control remains negative; characterized in that the control process also comprises: a stage involving the storage of a message sent by a terminal; a stage involving the receiving of at least one item of information from at least one external data server by means of communication through the Internet; and in that: the stage involving the condition control relating to the said stored message is at least partially performed using the information received from the external server.

The invention will be better understood and other features and advantages will be explained by the description below and the figures attached, given by way of example, where:

FIG. 1 schematically represents an example of a preferred embodiment of a system integrating a condition control device, terminals, messaging systems and data servers;

FIG. 2 schematically represents an example of a preferred embodiment of a message in which the condition field is integrated through the extending of the message format;

In FIGS. 1 and 2, the arrows represent exchanges of information. FIG. 2 solely represents an example of a conditional message whose format has been extended by adding a condition field. The condition control system calling on at least one external data server, and the associated control device and control process, may also be used to control a message encapsulated in an encapsulation element containing the condition field to be controlled. They may also be used to control a conventional message by means of conditions implemented in the communication network through user choices that are uniform for all the messages sent by the said users, however, this embodiment is far less advantageous as it lacks flexibility and simplicity for the setting of the conditions by the user transmitting the message.

FIG. 1 schematically represents an example of a preferred embodiment of a system integrating a condition control device, terminals, messaging systems and data servers; A first terminal 1, referred to hereafter as the transmitting terminal, is able to send a message 10 by attaching to it at least one condition 11. The terminal 1 is preferably a user terminal, in other words one able to send a message with any content to any recipient of its choice. The message 10 is sent to a receiving user 2. This receiving user 2 has at least one receiving terminal 21, but may have several, for example, also receiving terminals 22 and 23. The message 10 is usually sent to a receiving terminal, for example, the receiving terminal 21; however, this message 10 may under certain conditions be redirected to another of the receiving terminals of the receiving user 2, either to receiving terminal 22, or to receiving terminal 23. One or several messaging systems, here messaging systems 31, 32 and 33, may transmit messages between certain terminals. The message 10 is sent by the transmitting terminal 1 through at least one first messaging system, for example, the messaging system 31, able to transmit, to the second receiving terminal, for example, the receiving terminal 21, at least the message body of a message 10 from the first transmitting terminal 1. In the simplest case, the messaging system 31 routes the message 10 from the transmitting terminal 1 to the receiving terminal 21. It also possible for the message 10 to be sent through the messaging system 31 to the receiving user 2, but for it to be redirected before arriving at receiver 21, through another messaging system, for example, the receiving terminal 22. In this case, the message 10 transmitted by the messaging system, for example 32, to the receiving terminal 22 comes from the transmitting terminal 1, but it has not originally been transmitted through the messaging system 32, but through another messaging system, the messaging system 31. In a simple case, the entire message 10 may be transmitted to the receiving terminal. As at least the message body of the message 10 is to be transmitted, as it is the part that the transmitting user intended specifically for reading by the receiving user, it may happen that only a part of the message 10 is transmitted, for example, without the condition 11, such that the receiving user 2 is unable to read it.

Here, each receiving terminal has been represented as being coupled to a different messaging system, but several receiving terminals may also be coupled to the same messaging system. The transmitting terminal 1 for a message 10 may perhaps become the receiving terminal for another conditional message, but not necessarily. The terminal receiving the message 10 may perhaps also become the transmitting terminal for another conditional message, but not necessarily. Both the transmitting and receiving terminals may be, for example, a fixed or mobile telephone, a laptop or a PDA.

At least one condition control device 4 will perform a condition control, which will present a positive or negative result. If there is only one condition to be verified, if this condition is verified the condition control result will be positive, whereas if this condition is not verified, the control result will be negative. If there is a logical combination of several elementary conditions to be verified, if this logical combination of several elementary conditions is verified as a whole, the condition control result will be positive, whereas if this logical combination of several elementary conditions is not verified as a whole, the control result will be negative. A logical combination of several elementary conditions may be true as a whole even if not all the elementary conditions are true; this depends on the logical operators between the elementary conditions. If the control result is positive, the control device will allow the messaging system responsible for transmitting the message 10, or at least the message body of the message 10, to the receiving terminal, to transmit it effectively. If the control result is negative, the control device will prevent the messaging system responsible for transmitting the message 10, or at least the message body of the message 10, to the receiving terminal, from transmitting it effectively, at least during the time for which the condition result remains negative. More simply, the control device 4 allows the message 10 to, or prevents it from, continuing to be routed to the receiving terminal for which it is intended or to the receiving terminal towards which it is meant to be redirected, according to the condition control result. If the result is positive, the message 10 is transmitted. If the result is negative, the control device may either delete the message 10, or perform the condition control again later, one or several times, for example, periodically, until the condition control becomes positive, or further still, at the end of a timeout advantageously chosen by the transmitting user of transmitting terminal 1. The control device preferably has two parts, a part 41 that performs the condition control, and a part 42 that stores the messages that have at least one condition to be verified.

The condition control is performed by the control device 4 by means of at least one external data server. Here, the control device 4 may have access to several external data servers to help it to perform the control, which are the external data servers 51 to 54. An external data server is a server that is external to the control device 4, in other words, there is at least one link providing communication through the Internet between, on the one hand, the external server and, on the other hand, the control device 4. The control device 4 stores the message 10 sent by the transmitting terminal 1, at least for a sufficient time to allow the condition control to be performed. The control device 4 receives at least one item of information from at least one external server. The information receipt may arrive after message storage if the control device 4 requests this after receipt of the message. If the external server regularly sends updated information to the control device 4, the necessary information may already be available for the control device 4 when it receives the message 10. In the simplest case, it receives information from an external server. In more complex cases, it may receive several items of information from a server, or one or several items of information from several servers. The control device 4 at least partially performs the condition control relating to the said message 10 stored by means of the information received from the external server(s). The control is at least partially performed by means of this/these item(s) of information received from the external server(s), as the condition control may also bring into play one or several other items of information, such as, for example, an item of information internal to the control device 4, or an item of information contained in the message 10. The, or at least one of, the conditions is preferably mandatory, at least for a certain time; however, it is possible that one or some conditions, or even all, may be optional, in the sense that their verification is not required for the transmission of the message if the control result cannot be established, for lack of information.

In another embodiment not represented in FIG. 1, the control device is in fact integrated in a messaging system and is presented in the form of a condition control application layer, in which case the changing of the messaging system during routing from the transmitting terminal to the receiving terminal is not possible. The data server is in this case external to the messaging system, in other words, there is at least one link providing communication through the Internet between, on the one hand, the external server, and on the other hand, the messaging system. The condition control application layer either stores itself, or has stored by the messaging system, the message 10 sent by the transmitting terminal 1, until the condition control is performed.

Preferably, the condition, or at least one of the conditions to be controlled, relates to the receiving terminal. This may also be a condition relating more generally to the receiving user themselves.

Preferably, the system comprises at least one other messaging system able to transmit a message of a different type to that of the first messaging system. For example, indeed, if the message 10 is intended for the receiving user 2, and more specifically the receiving terminal 21 coupled to the same messaging system 31 as the transmitting terminal 1, this message 10, or at least the message body of this message 10, may be redirected through another messaging system 33, intended for a receiving terminal 23 that is coupled with it. Different examples of message types may be SMS, MMS, emails, voice messages with a condition field that would also be voice-based, etc.

In the case of transmission between a transmitting terminal using a messaging system (for example, email) and a receiving terminal using another messaging system (for example, SMS), there may be transcription from one format to another to allow transmission of the message.

Preferably, either at the request of the transmitting terminal 1, or on the expiry of a predetermined period, in the case of a negative control result, a failure message is sent to the transmitting terminal 1. Thus, in the first case, the transmitting user knows where they stand with regard to the fate of their message 10, and in the second case, in the case of conditions that are too difficult to meet, it is ensured that the control device 4, and more specifically part 42 storing the conditional messages, is not overwhelmed by messages with conditions that were never met, as once the failure message has been sent and the transmitting user has been informed, the control device can delete the message 10.

Preferably, the system comprises at least one other external data server able to be consulted during the condition control, for the controlling of the same condition. This improves the system's reliability, as if an external server is faulty, the condition control may nevertheless be performed, thanks to a spare server, which costs the system nothing as it already exists in the Internet network.

Preferably, the link to the external server is provided by means of a subscription to the external server, which allows the control device to be informed once an unverified condition becomes verified. Otherwise, it is necessary for it to make numerous consultations either close together or far apart, with the risk of either only transmitting the message a long time after the conditions have been met, or, if several conditions must be met, the risk that these will never be met simultaneously for a sufficiently long time to lead to a positive condition control result.

The external server is a server that is not controlled by the control device 4. It is a conventional server that belongs to the Internet network and may, at least technically, although sometimes authorization may be necessary, be accessed by other Internet users. Several examples of external data servers will now be given. The external server, or at least one of the external servers, is, for example, a clock. An example of a condition is only transmitting the message 10 the day after it has been sent. The external server, or at least one of the external servers, is, for example, a receiving terminal localization server. An example of a condition is only transmitting the message 10 if the receiving terminal is in the city of New York. Clocks and localization servers are in practice the most useful server types. Other servers are, however, possible. The external server, or at least one of the external servers, is, for example, a biometric sensor associated with the receiving terminal. Information on the stress level of the receiving user allows, for example, the transmitting of a message to the user only when they are in a fit psychological state to receive it. The external server, or at least one of the external servers, is, for example, a weather server. An example of a condition is only transmitting the message if there is snow in Paris. The external server, or at least one of the external servers, is a psychological database fed by the user of the receiving terminal. An example of a condition is only transmitting the message 10 if the receiving user has indicated that they are in a good mood. One or several conditions to be controlled may also be controlled internally within the control device, by means of information available in the control device itself, but at least one condition to be controlled is controlled by means of an external server.

FIG. 2 schematically represents an example of a preferred embodiment of a message in which the condition field is integrated through the extending of the message format. The message contains a message body 102, a transmitting field not represented here as it is implicit, and a receiving field 100. Here, when the message is composed, only the fields that the transmitting user is likely to complete are represented, namely at least the receiving field 100 and the message body 102. The message may also contain other optional fields to be completed by the transmitter if they desire, such as, for example, a message subject field 101 or a complementary message data field 103. The message is intended to be sent by a transmitter, transmitting user or transmitting terminal, associated with the transmitting field, to a receiver, receiving user or receiving terminal, associated with the receiving field.

The message also contains a condition field 104 that is intended to be completed by the associated transmitter and may contain the parameter(s) representative of at least one elementary condition, in particular the condition 11 of the FIG. 1, which is intended to be verified by a server associated with the condition field 104, in particular the control device of the FIG. 1. The associated server is separate from the associated receiver; indeed, the associated server is not part of the associated receiver as the associated receiver should not be likely to control this associated server or modify messages that it has not transmitted. Indeed, the associated receiver should not be able to alter the condition(s) set by the associated transmitter for the transmission of the message, or in any case in opposition to the wishes of the transmitting user. The associated server is intended to transmit at least the message body to the associated receiver if the elementary condition is verified, the said associated server being intended to not transmit the message body to the associated receiver if the elementary condition is not verified, at least for as long as the elementary condition has not been verified. Indeed, if the elementary condition is not verified, the condition control may preferably be performed severally times, perhaps periodically, in the case of a failure the first time. This new condition control attempt is performed, either until the elementary condition becomes verified, or advantageously for a certain time only after which the message may simply be deleted by the associated server, a failure message from the associated server possibly informing the associated transmitter that the message transmission attempt has failed.

The condition field 104 may consist of the simple case of only requiring the verification of an elementary condition. Other more complex cases may of course be envisaged, such as the case where the condition field 104 may contain the parameter(s) representative of at least one logical combination of several elementary conditions that is intended to be verified by a server associated with the condition field. The associated server is therefore intended to transmit at least the message body to the associated receiver if the logical combination is verified, the said associated server being intended not to transmit the message body to the associated receiver if the logical combination is not verified. If the logical combination is not verified, one or several new attempts, as in the case of the elementary condition described above, remain possible. The logical operators between elementary conditions may preferably be several different types; they are therefore advantageously explained in the condition field 104, thus allowing a greater variety and flexibility in the creation of the logical combination of elementary conditions. The logical operator(s) may also be implicit, either if only one is possible, for example the operator AND, or if, for at least one or several elementary conditions, the type of each of these elementary conditions controls a single logical operator and no others. Other, non-limitative, examples of logical operators between elementary conditions may be OR, exclusive OR, AND NOT, etc., or more sophisticated operators such as UNLESS. For example, transmitting the message after 14 hours or before this time if the associated receiver is already in Paris. For example, transmitting to the associated receiver once they are in Paris, unless it snows or they are too stressed.

The preferred example in FIG. 2 shows an embodiment in which the condition field 104 is an extension of the message body 102. Indeed, the message has a format in which both the message body 102 and the condition field 104 are included. This embodiment, which is the simplest to use, nevertheless requires considerable effort to set up, as it involves defining a new format that will make the message understandable and processable by the associated server and must allow the messaging system to continue transmitting the message. If the control device in FIG. 1 is integrated in the messaging system in the form of an application layer of this messaging system, this application layer may take care of making the new format understandable to the messaging system without having to substantially modify it. Another embodiment, not represented in FIG. 2, consists of including the condition field in an encapsulation of the message body. This embodiment allows simpler implementation as it does not modify the message's original format, making use less optimal however.

Preferably, the condition field 104 is never intended to be transmitted with the message body 102 to the associated receiver. Thus, the confidentiality of the transmitting user's intention is maintained with regard to the receiving user. It may even be envisaged, according to the user's wishes, for some elementary conditions to be hidden from the receiving user when the message is transmitted, with other elementary conditions remaining visible to the receiving user. In this case also, only part of the message is actually transmitted.

Preferably, the condition field comprises three sub-fields for at least one, some or all the elementary conditions, namely a type, a reference and an operator, and the said condition is verified, if the type value verifies the reference operator type relationship, in other words if the comparison between the type and the reference by means of the operator gives a positive result. These sub-fields are not mandatory because, as we have seen above, both for the condition type and the logical operator in particular, these may be implicit and may not need to be included in the condition field 104, in particular if the message is created by the transmitter. More specifically, the condition field 104 preferably contains three sub-fields, a first condition type sub-field, a second condition value sub-field and a third operator sub-field. Elementary condition verification consists of performing the following operation: during the control, comparing the effective value at the time of the control or around this time, of the condition type contained in the first sub-field on the one hand and the value contained in the second sub-field on the other hand, by means of the operator contained in the third sub-field, with the result of this comparison causing the transmission of the message to be permitted or prohibited. For example, for the content of the following three sub-fields, "time", "2" and "greater than", the corresponding elementary condition will be verified if it is greater than 2.00 pm. For example, for the content of the following three sub-fields, "heartbeats", "120", "less than", the elementary condition is verified if the biometric sensor associated with the receiver indicates that the number of heartbeats of the receiving user is less than 120 beats per minute. For example, for the content of the following three sub-fields, "place", "Bavaria", "inclusion", the corresponding elementary condition will be verified if the receiver is in a location within Bavaria in Germany.

To summarize, and more generally speaking, the message comprising a message body, a transmitting field and a receiving field, also contains a condition field that it is completed by the transmitter and allows a server that is separate from the receiver to transmit or not transmit at least the message body to the receiver. It is the result of the condition field's evaluation by this server, which may in particular be the control device in FIG. 1 or a messaging system application layer, on which is based the permission or prohibition to transmit the message, or more specifically at least part of the message including the message body, or even in an extreme case reduced to the message body.

Examples of condition types will now be given. For example, the elementary condition, or at least one of the elementary conditions, is a date condition. An example of such an elementary condition is transmitting the message on Jan. 1, 2006. For example, the elementary condition or at least one of the elementary conditions is a localization condition relating to the associated receiver. An example of such an elementary condition is transmitting the message once the receiver is in the train midway between Paris and Vienna. For example, the elementary condition, or at least one of the elementary conditions, is a biometric condition from a biometric sensor associated with the associated receiver. An example of such an elementary condition is transmitting a prerecorded alarm message if the transmitting user's pulse can no longer be detected. For example, the elementary condition, or at least one of the elementary conditions, is a weather condition. An example of such an elementary condition is transmitting the message once a storm affecting a given village has ended. For example, the elementary condition, or at least one of the elementary conditions, is a psychological state condition from a database completed by the user of the associated receiver. An example of an elementary condition is transmitting the message if the receiving user indicates their wish to once more receive humorous messages.

Several languages may be used to complete the message condition field 104. For example, XML allows better data structuring, which is particularly useful if the condition field 104 contains a combination of elementary conditions.

Other syntaxes are possible based on logical rules written in higher level languages based on XML, such as SWRL.

An example of the contents of a condition field written in XML format is given below:

```
<MessageCondition>
    <Or>
        <! Send if at least one of the conditions is met>
        <ElementaryCondition Name="Time"
        Value="051112132500" Operator="=="/>
        <! CurrentTime is equal to 12 Nov. 05 at 13h25mn>
        <ElementaryCondition Name="Time"
        Value="(051225000100, 060101000100)"
        Operator=" isIncluded"/>
        <! CurrentTime is between 25 Dec 05 at 00h01 mn and 01
        Jan 06 at 00h01 mn >
        <And>
            <Not>
                <ElementaryCondition Name="Weather"
                Value="snowy" Operator="=="/>
            </Not>
            <ElementaryCondition Name="GPS-Localization"
            Value="(37.5, 42.3)"
Operator="=="/>
        </And>
    </Or>
</MessageCondition>
```

The invention claimed is:

1. A system comprising:
a first terminal (1);
a second terminal (21 or 22 or 23);
at least a first messaging system (31 or 32 or 33) able to transmit, to the second terminal, at least a message body of a message (10) from the first terminal;
at least one condition control device (4) controlling at least one condition (11), at least once, the control device allowing the first messaging system to transmit to the second terminal at least the message body of the message if a condition control result is positive, the control device preventing the first messaging system from transmitting to the second terminal at least the message body of the message if the condition control result is negative, at least during a time for which the condition control result remains negative;
characterized in that the system also comprises:
at least one data server (51 or 52 or 53 or 54) external to the control device;
at least one link providing communication through the Internet between on the one hand at least one of the at least one external data server, and on the other hand the control device;
and in that the condition control device is operative to:
store the message sent by the first terminal;
receive at least one item of information from at least one of the at least one external data server; and
at least partially perform the condition control relating to the stored message according to the information received from the external data server without regard to content of portions of the message other than a condition field including at least a type, a reference and an operator, if the condition field is included.

2. A system comprising:
a first terminal (1);
a second terminal (21 or 22 or 23);
at least a first messaging system (31 or 32 or 33) able to transmit, from the first terminal to the second terminal, at least a message body of a message (10), the first messaging system having an application layer controlling at least one condition (11) at least once;
the application layer allowing the first messaging system to transmit to the second terminal at least the message body of the message if a condition control result is positive, the application layer preventing the first messaging system from transmitting to the second terminal at least the message body of the message if the condition control result is negative, at least during the time for which the condition control result remains negative;
characterized in that the system also comprises:
at least one data server (51 or 52 or 53 or 54) external to the first messaging system;
at least one link providing communication through the Internet between on the one hand the at least one external data server and on the other hand the first messaging system;
and in that the application layer is designed to:
store, or have stored by the first messaging system, the message sent by the first terminal;
receive at least one item of information from the at least one external data server; and
at least partially perform the condition control relating to the stored message according to the information received from the external data server without regard to portions of the message other than a condition field including at least a type, a reference and an operator, if the condition field is included.

3. The system according to claim 1, characterized in that the condition, or at least one of the conditions to be controlled, relates to the second terminal or the second terminal's user.

4. The system according to claim 1, characterized in that the system comprises at least one other external data server (51 or 52 or 53 or 54) that is able to be consulted when the condition is controlled, for the controlling of the same condition.

5. The system according to claim 1, characterized in that the system comprises at least one other messaging system (31 or 32 or 33) able to transmit a message of a type other than that of the first messaging system.

6. The system according to claim 1, characterized in that the link to the at least one external server is provided by means of subscription to the at least one external server.

7. The system according to claim 1, characterized in that, either at the request of the first terminal, or on the expiry of a predetermined period, if the control result is negative, a failure message is sent to the first terminal.

8. The system according to claim 1, characterized in that at least one of the at least one external server is a clock.

9. The system according to claim 1, characterized in that at least one of the at least one external server is a localization server for the second terminal.

10. The system according to claim 1, characterized in that at least one of the at least one external server is a biometric sensor associated with the second terminal.

11. The system according to claim 1, characterized in that at least one of the at least one external server is a weather server.

12. The system according to claim 1, characterized in that the external server, or at least one of the external servers, is a psychological database completed by the second terminal's user.

13. A device controlling at least one condition, at least once, the device comprising:
- a controller device operative to, at least once, allow a messaging system to transmit from a first terminal to a second terminal at least a message body of a message sent by the first terminal if a condition control result is positive;
- prevent the messaging system from transmitting to the second terminal at least the message body of the message sent by the first terminal if the condition control result is negative, at least during a time for which the condition control result remains negative;
- characterized in that the controller device is also designed to:
- be linked through the Internet to at least one data server external to the controller device;
- and in that the condition controller device is also designed to: store the message sent by the first terminal;
- receive at least one item of information from the at least one external data server; and
- at least partially perform the condition control relating to the stored message according to the information received from the external data server without regard to content of portions of the message other than a condition field including at least a type, a reference and an operator, if the condition field is included.

14. A method for controlling in a messaging system, the method comprising:
at least once,
- allowing, by a condition control device, a messaging system to transmit at least a message body of a message from a first terminal to a second terminal if a condition control result is positive;
- preventing the messaging system from transmitting to the second terminal at least the message body of the message sent by the first terminal if the condition control result is negative, at least during the time for which the condition control remains negative;

wherein the method further includes:
- storing by the messaging system, the message sent by the first terminal;
- receiving, by the condition control device, at least one item of information from at least one external server through the Internet; and
- at least partially performing the condition control relating to the stored message according to the information received from the external server without regard to content of portions of the message other than a condition field including at least a type, a reference and an operator, if the condition field is included.

15. A process controlling at least one condition, at least once, the process comprising;
- a condition control stage which at least once, in the case of a positive condition control result, a condition control device allows a messaging system to transmit at least a message body of a message from a first terminal to a second terminal, and which, if the condition control result is negative, prevents the messaging system from transmitting to the second terminal at least the message body of the message sent by the first terminal, at least during the time for which the condition control result remains negative;
- characterized in that the control process also comprises:
- a stage involving the storage of the message sent by the first terminal;
- a stage involving the receiving of at least one item of information from at least one external data server by means of communication through the Internet;
- and in that:
- the stage involving the condition control relating to the stored message is at least partially performed using the information received from the external data server and is performed without regard to content of portions of the message other than a condition field including at least a type, a reference and an operator, if the condition field is included.

* * * * *